United States Patent
Staib et al.

(10) Patent No.: US 10,422,765 B2
(45) Date of Patent: Sep. 24, 2019

(54) DIFFUSION LAYER FOR AN ENZYMATIC IN VIVO SENSOR

(71) Applicant: Roche Diabetes Care, Inc., Indianapolis, IN (US)

(72) Inventors: Arnulf Staib, Heppenheim (DE); Marcel Thiele, Mannheim (DE); Karl-Heinz Koelker, Gruenstadt (DE); Ewald Rieger, Bobenheim-Roxheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 540 days.

(21) Appl. No.: 14/027,493

(22) Filed: Sep. 16, 2013

(65) Prior Publication Data

US 2014/0018653 A1   Jan. 16, 2014

Related U.S. Application Data

(63) Continuation of application No. PCT/EP2012/055406, filed on Mar. 27, 2012.

(30) Foreign Application Priority Data

Mar. 28, 2011   (EP) .................... 11160007

(51) Int. Cl.
   *C12Q 1/00*   (2006.01)
   *A61B 5/145*   (2006.01)
   (Continued)

(52) U.S. Cl.
   CPC ....... *G01N 27/3272* (2013.01); *A61B 5/1486* (2013.01); *A61B 5/14532* (2013.01);
   (Continued)

(58) Field of Classification Search
   CPC .............. A61B 5/14532; A61B 5/1486; A61B 5/14865; C12Q 1/006; C12Q 1/002; G01N 27/3272
   See application file for complete search history.

(56) References Cited

U.S. PATENT DOCUMENTS 3,542,662 A    11/1970   Hicks et al.
4,292,301 A *  9/1981   Keith .................. A61K 9/70
                                                           424/449

(Continued)

FOREIGN PATENT DOCUMENTS

EP    1621636 A1    2/2006
EP    2163190 A1    3/2010

(Continued)

OTHER PUBLICATIONS

Lu et al, Simple Fabrication of a Highly Sensitive Glucose Biosensor Using Enzymes Immobilized in Exfoliated Graphite Nanoplatelets Nafion Membrane, Chem. Mater. 2007, 19, 6240-6246.*

(Continued)

*Primary Examiner* — Patricia Mallari
*Assistant Examiner* — Tho Q Tran
(74) *Attorney, Agent, or Firm* — Woodard, Emhardt, Henry, Reeves & Wagner, LLP

(57) ABSTRACT

Electrode systems are disclosed for measuring the concentration of an analyte under in vivo conditions, where the systems includes an electrode with immobilized enzyme molecules and an improved diffusion barrier that controls diffusion of the analyte from body fluid surrounding the electrode system to the enzyme molecules. Methods of making and using the system also are disclosed.

25 Claims, 7 Drawing Sheets

(51) Int. Cl.
*A61B 5/1486* (2006.01)
*G01N 27/327* (2006.01)

(52) U.S. Cl.
CPC .......... *A61B 5/14865* (2013.01); *C12Q 1/002* (2013.01); *C12Q 1/006* (2013.01)

(56) References Cited

U.S. PATENT DOCUMENTS

| | | | |
|---|---|---|---|
| 4,298,002 A | | 11/1981 | Ronel et al. |
| 4,418,148 A | * | 11/1983 | Oberhardt .......... G01N 27/3271 204/296 |
| 5,777,060 A | | 7/1998 | Van Antwerp |
| 6,001,067 A | | 12/1999 | Shults et al. |
| 6,024,848 A | * | 2/2000 | Dufner ...................... C25B 9/08 204/252 |
| 6,270,788 B1 | | 8/2001 | Koulik et al. |
| 6,497,729 B1 | * | 12/2002 | Moussy ............... A61B 5/0031 424/423 |
| 6,751,491 B2 | | 6/2004 | Lew et al. |
| 7,232,573 B1 | | 6/2007 | Ding |
| 2003/0217966 A1 | * | 11/2003 | Tapsak ................. B01D 69/141 210/500.21 |
| 2004/0096505 A1 | | 5/2004 | Woerly |
| 2004/0106166 A1 | | 6/2004 | Matsumoto |
| 2005/0245795 A1 | * | 11/2005 | Goode, Jr. ........... A61B 5/0031 600/302 |
| 2005/0256253 A1 | * | 11/2005 | Parker ...................... C08F 2/38 524/543 |
| 2006/0015083 A1 | * | 1/2006 | Munro .................. A61L 15/425 604/367 |
| 2006/0025550 A1 | * | 2/2006 | Liu ......................... C12Q 1/002 526/319 |
| 2006/0067908 A1 | | 3/2006 | Ding |
| 2006/0275857 A1 | | 12/2006 | Kjaer et al. |
| 2006/0275859 A1 | * | 12/2006 | Kjaer ..................... C12Q 1/002 435/25 |
| 2007/0093704 A1 | | 4/2007 | Brister et al. |
| 2007/0213611 A1 | | 9/2007 | Simpson et al. |
| 2007/0244379 A1 | | 10/2007 | Boock et al. |
| 2008/0027287 A1 | | 1/2008 | Shah et al. |
| 2008/0035479 A1 | * | 2/2008 | Liu ......................... C12Q 1/002 204/403.14 |
| 2010/0030052 A1 | | 2/2010 | Bommakanti et al. |
| 2010/0116681 A1 | | 5/2010 | Papadimitrakopoulos et al. |
| 2011/0033517 A1 | | 2/2011 | Glauser et al. |
| 2012/0097554 A1 | | 4/2012 | Sha et al. |
| 2012/0213986 A1 | * | 8/2012 | Kowalewski ............ H01B 1/04 428/304.4 |

FOREIGN PATENT DOCUMENTS

| | | |
|---|---|---|
| WO | 1992013271 A1 | 8/1992 |
| WO | 1993015651 A1 | 8/1993 |
| WO | 1997/019344 A1 | 5/1997 |
| WO | 2006/058779 A1 | 6/2006 |
| WO | 2007/147475 A1 | 12/2007 |
| WO | 2008109739 A1 | 9/2008 |
| WO | 2010/028708 A1 | 3/2010 |
| WO | 2012019083 A2 | 2/2012 |

OTHER PUBLICATIONS

Tauer et al, On the role of hydrophilicity and hydrophobicity in aqueous heterophase polymerization, 2005, Polymer, 46: 1003-1015.*
Ruzette (Block copolymers: Copolymers close the loop, 2002, Nature Materials, 1: 85-87).*
Penzel et al (The glass transition temperature of random copolymers: 1. Experimental data and the Gordon-Taylor equation, 1997, Polymer, 38(2): 325-337).*
Carr, Louisa R. et al., "Functionalizable and nonfouling zwitterionic carboxybetaine hydrogels with a carboxybetaine dimethacrylate crosslinker," Biomaterials, 2011, pp. 961-968, vol. 32.
Zhang, Lei et al., "Zwitterionic hydrogels implanted in mice resist the foreign-body reaction," Nature Biotechnology, Jun. 2013, pp. 553-556, vol. 31, No. 6.
Abraham, Sheena et al., "Molecularly engineered p(HEMA)-based hydrogels for implant biochip biocompatibility," Biomaterials, 2005, pp. 4767-4778, vol. 26.
BioInteractions Ltd. Adapt(tm) Biostable Drug Delivery Platform, 1 page, United Kingdom.
Boeker, Alexander et al., "Nanoscopic Surface Patterns from Functional ABC Triblock Copolymers," Marcomolecules, 2001, pp. 7477-7488, vol. 34.
Boztas, Ali Ozgur and Guiseppi-Elie, Anthony, "Immobilization and Release of the Redox Mediator Ferrocene Monocarboxylic Acid from within Cross-Linked p(HEMA-co-PEGMA-co-HMMA) Hydrogels," Biomacromolecules, 2009, pp. 2135-2143, vol. 10.
Ishihara, Kazuhiko et al., "Preparation of Phospholipid Polymers and Their Properties as Polymer Hydrogel Membranes," Polymer Journal, 1990, pp. 355-360, vol. 22, No. 5.
Lewis, Andrew L. et al., "Synthesis and characterisation of phosphorylcholine-based polymers useful for coating blood filtration devices," Biomaterials, 2000, pp. 1847-1859, vol. 21.
Mang, A. et al., "Biocompatibility of an Electrochemical Sensor for Continuous Glucose Monitoring in Subcutaneous Tissue," Diabetes Technology & Therapeutics, Nov. 2005, pp. 163-173, No. 7.
Morais, Jacqueline M. et al., "Biomaterials/Tissue Interactions: Possible Solutions to Overcome Foreign Body Response," The AAPS Journal, Jun. 2010, pp. 188-196, vol. 12, No. 2.
Nakabayashi, N. and Iwasaki, Y., "Copolymers of 2-methacryloyloxyethyl phosphorylcholine (MPC) as biomaterials," Bio-Medical Materials and Engineering, 2004, pp. 345-354, vol. 14.
Uchiyama, Tomoaki et al., "Biocompatible polymer alloy membrane for implantable artificial pancreas," Journal of Membrane Science, 2002, pp. 39-48, vol. 208.
Wang, Yan et al., "Polymeric 'smart' coatings to prevent foreign body response to implantable biosensors," Journal of Controlled Release, 2013, http://dx.doi.org/10.1016/jjconrel.2012.12.028.
Yin, Dehui and Horiuchi, Shin, "Lateral Assembly of Metal Nanoparticles Directed by Nanodomain Control in Block Copolymer Thin Films," Chemistry of Materials, 2005, pp. 463-469, vol. 17.
Interlocutery Decision in Opposition Proceedings re: EP12710734.0 dated Dec. 18, 2017.
Berrocal et al., 'Reducing the Thrombogenicity of Ion-Selective Electrode Membranes through the Use of a Silicone-Modified Segmented Polyurethane', Anal. Chem., 2001, 73 (21), pp. 5328-5333 DOI: 10.1021/ac010375i Publication Date (Web): Sep. 28, 2001.
Boker et al., 'Nanoscopic Surface Patterns from Functional ABC Triblock Copolymers', Macromolecules, 2001, 34 (21), pp. 7477-7488 DOI: 10.1021/ma002198d, Publication Date (Web) Sep. 12, 2001.
Huntsman, A guide to Thermoplastic Polyurethanes (TPU).
Product Description PurSil (2007), 'Thermoplastic Silicone Polyether Urethane', The Polymer Technology Group.
Product Description PurSil AL (2006), 'Aliphatic Thermoplastic Silicone Polyether Urethane', The Polymer Technology Group.
Ring et al., 'Source-based nomenclature for copolymers (Recommendation 1985): International Union of Pure and Applied Chemistry (IUPAC) Macromolecular Division Commission on Macromolecular Nomenclature', Polymer Science U.S.S.R.; vol. 28; Issue 5, 1986, pp. 1223-1229.
Shaikh et al., 'Engineering Stent Based Delivery System for Esophageal Cancer Using Docetaxel', Mol. Pharmaceutics, 2015, 12 (7), pp. 2305-2317 DOI: 10.1021/mp500851u Publication Date (Web). May 2, 2015.
Verstraete et al., 'Hydrophilic thermoplastic polyurethanes for the manufacturing of highly dosed oral sustained release matrices via hot melt extrusion and injection molding', International Journal of Pharmaceutics, vol. 506, Issues 1-2, Jun. 15, 2016, pp. 214-221.

(56) References Cited

OTHER PUBLICATIONS

Ward et al.., 'Environmentally Induced Surface angement of Polyurethanes using SFG, AFM, XPS, and Contact Angle Goniometry', The Polymer Technology Group, Presented at the 25th Annual Meeting of the Society for Biomaterials, Apr. 29-May 1, 1999, Providence, Rhode Island, USA.

Zhang et al., 'Environment-Induced Surface Structural Changes of a Polymer:? An in Situ IR + Visible Sum-Frequency Spectroscopic Study', J. Phys. Chem. B, 1997, 101 (44), pp. 9060-9064 DOI: 10.1021/jp9718358: Publication Date (Web): Oct. 30, 1997.

Indian Application No. 6960/CHENP/2014 to F. Hoffmann La Roche AG, Office Action dated Feb. 7, 2019. 6 pages.

U.S. Appl. No. 14/486,402 to Roche Diabetes Care, Inc., Office Action dated Sep. 5, 2017. 11 pages.

U.S. Appl. No. 14/486,402 to Roche Diabetes Care, Inc., Office Action dated Jul. 24, 2018. 14 pages.

Further submissions in Opposition Proceedings dated Jul. 25, 2017 and Jul. 28, 2017 in EP 2 697 388 B1.

Grounds of Appeal at Apr. 30, 2018 in EP 2 697 388 B1.

Interlocutory decision in Opposition Proceedings dated Dec. 18, 2017 in EP 2 697 386 B1.

International Prelimenary Report on Patentability dated Mar. 21, 2013 in PCT/EP2012/055406.

International Search and Written Opinion dated May 4, 2012 issued in PCT/EP2012/055406.

Notice of Opposition filed on Feb. 19, 2016 in EP 2 697 388 B1.

Office Action in related India application IN6928/CHENP/2013 dated Feb. 2, 2018.

Reply to Appeal dated Aug. 9, 2018 in EP 2 697 388 B1.

Reply to Appeal dated Aug. 17, 2018 in EP 2 697 388 B1.

Reply to Notice of Opposition dated Sep. 26, 2016 in EP 2 697 388 B1.

Statement of Grounds of Appeal dated Apr. 16, 2018 in EP 2 697 388 B1.

\* cited by examiner

DIFFUSION LAYER FOR AN ENZYMATIC IN VIVO SENSOR

CROSS-REFERENCE TO RELATED APPLICATIONS

This patent application is a continuation of Int'l Patent Application No. PCT/EP2012/055406; filed 27 Mar. 2012, which claims the benefit of EP Patent Application No. 11160007.8; filed 28 Mar. 2011. Each patent application is incorporated herein by reference as if set forth in its entirety.

TECHNICAL FIELD

The invention relates generally to engineering and electrochemistry, and more particularly to an electrode system for measuring a concentration of an analyte under in vivo conditions, where the system includes a working electrode with immobilized enzyme molecules and an improved diffusion barrier that controls diffusion of the analyte from body fluid surrounding the electrode system to the immobilized enzyme molecules.

BACKGROUND

Sensors with implantable or insertable electrode systems facilitate measurements of physiologically significant analytes such as, for example, lactate or glucose in an individual's body. The working electrodes of systems of this type have electrically conductive enzyme layers in which enzyme molecules are bound and release charge carriers by catalytic conversion of the analyte. In the process, an electrical current is generated as a measuring signal whose amplitude correlates to the analyte's concentration. Such electrode systems are disclosed in, for example, Int'l Patent Application Publication Nos. WO 2007/147475 and WO 2010/028708.

The working electrodes of the electrode system typically are provided with a diffusion barrier to control diffusion of the analyte to be determined from the body fluid or tissue surrounding the electrode system to the enzyme molecules that are immobilized in the enzyme layer. According to Int'l Patent Application No. WO 2010/028708, the diffusion barrier of the electrode system is a solid solution of at least two different polymers, preferably acrylates. The polymers may be copolymers such as, for example, copolymers of methyl methacrylate and hydroxyethyl methacrylate or copolymers of butyl methacrylate and hydroxyethyl methacrylate.

Likewise, Int'l Patent Application Publication No. WO 2007/147475 discloses a diffusion barrier made from a polymer having a zwitterionic structure. An example of such a polymer is poly(2-methacryloyloxyethyl phosphorylcholine-co-n-butylmethacrylate). The zwitterionic polymer may be mixed with another polymer such as, for example, polyurethane.

The use of polymer or copolymer mixtures, however, has drawbacks in that the preparation of the mixture and its application to the sensor is tedious and potentially problematic. Usually, the polymers to be mixed are individually dissolved and the resulting solutions are thereafter mixed in the desired ratio. This may result in precipitation of one of the components and consequently in workability problems (e.g., in a spraying process). Increased difficulties occur when the mixture includes a polymer with ionic characteristics (i.e., when one of the polymers to be mixed includes a monomer having anionic or cationic groups). The presence of such charged groups has a strong effect on the solubility, making it difficult to find a solvent suitable for both the charged polymer and an uncharged polymer.

Int'l Patent Application Publication No. WO 2006/058779 discloses an enzyme-based sensor with a combined diffusion and enzyme layer including at least one polymer material, and particles carry an enzyme, where the particles are dispersed in the at least one polymer material. The polymer may be hydrophilic as well as hydrophobic polymer chain sequences such as, for example, the polymer may be a high or low water uptake polyether-polyurethane copolymer. The use of block copolymers having at least one hydrophilic block and at least one hydrophobic block as a diffusion layer is not disclosed.

EP Patent Application Publication No. 2163190 discloses an electrode system for measuring an analyte concentration in vivo that includes a counter electrode with an electric conductor and a working electrode with an electric conductor on which an enzyme layer having immobilized enzyme molecules is localized. A diffusion barrier controls diffusion of the analyte from surrounding body fluids to the immobilized enzyme molecules. The diffusion barrier includes hydrophilized polyurethanes obtained by polycondensation of 4,4'-methylene-bis-(cyclohexylisocyanate) and diol mixtures that may be polyethyleneglycol and polypropyleneglycol. The hydrophilic polyurethane layer may be covered with a spacer such as, for example, a copolymer of butyl methacrylate and 2-methacryloyloxyethyl-phosphoryl choline. The use of block copolymers having at least one hydrophilic block and at least one hydrophobic block as a diffusion layer is not disclosed.

For the foregoing reasons, there is a need for electrode systems having improved diffusion barriers/cover layers.

BRIEF SUMMARY

It is an object of the present disclosure to provide a diffusion barrier on an electrode system of an enzymatic in vivo sensor that provides desirable physico-chemical characteristics and that can be manufactured easily.

This object is met by a diffusion barrier including a single block copolymer having at least one hydrophilic block and at least one hydrophobic block. The hydrophilic and hydrophobic blocks are covalently linked to each other. In certain embodiments, the blocks are (meth)acrylate polymer blocks.

The block-copolymer-based diffusion barrier provides the following physico-chemical characteristics:
  (i) permeability of the diffusion barrier for the analyte to be determined;
  (ii) permeability characteristics of the diffusion barrier that are suitable for the short-term behavior (i.e., wettability) and the long-term behavior (i.e., sensor drift) of the electrode;
  (iii) mechanical flexibility of the diffusion barrier, which allows manufacture of in vivo sensors with extended multiple electrodes; and/or
  (iv) efficient incorporation of ionic groups into the diffusion layer (i.e., the density of cationic or anionic charges within the polymer can be efficiently adjusted, which is relevant for repulsion or attraction of charged analytes, and/or control of cell adhesion such as, for example, of monocytes from the surrounding body fluid or tissue).

One aspect therefore includes an electrode system for measuring concentration of an analyte under in vivo conditions. The system includes an electrode with immobilized enzyme molecules and a diffusion barrier that controls diffusion of the analyte from an exterior of the electrode system to the immobilized enzyme molecules, where the diffusion barrier includes a block copolymer having at least one hydrophilic block and at least one hydrophobic block as described herein.

In one embodiment, the diffusion barrier includes a single (i.e., only one) block copolymer having at least one hydrophilic block and at least one hydrophobic block (i.e., further polymers or copolymers may be absent). In another embodiment, the diffusion barrier is a single block copolymer having at least one hydrophilic block and at least one hydrophobic block.

The electrode system described herein can be incorporated into a sensor that is inserted or implanted into a body such as, for example, a mammalian body, including a human body. The electrode system can be adapted for measuring a desired analyte in body fluid and/or body tissue such as, for example, in an extracellular space (interstitium), in blood or lymph vessels or in a transcellular space.

The inserted or implanted electrode system is suitable for short-term application (i.e., about 3-14 days) or for long-term application (i.e., about 6-12 months). During the insertion or implantation period, a desired analyte may be determined by continuous or discontinuous measurements.

The electrode system can be part of an enzymatic, non-fluidic (ENF) sensor, where enzymatic conversion of the analyte is determined. In this embodiment, the sensor includes a working electrode (WE) with immobilized enzyme molecules for converting the analyte, which results in generation of an electrical signal. The enzymes may be present in a layer covering the electrode. Additionally, the system can include redox mediators and/or electro-catalysts, as well as conductive particles and pore formers. This type of electrode is described in, for example, Int'l Patent Application Publication No. WO 2007/147475.

The area of the WE is the sensitive area of the sensor. This sensitive area includes the diffusion barrier to control diffusion of the analyte from the exterior (e.g., body fluid and/or tissue surrounding the electrode system) to the enzyme molecules. The diffusion barrier can be, for example, a cover layer covering the enzyme layer (i.e., an enzyme-free layer). However, it is feasible that diffusion-controlling particles can be incorporated into the enzyme layer to serve as the diffusion barrier. For example, pores of the enzyme layer can be filled with the polymer that controls diffusion of analyte molecules.

In some embodiments, the thickness of the diffusion barrier can be from about 2 μm to about 20 μm, from about 2 μm to about 15 μm, or from about 5 μm to about 20 μm. Alternatively, the thickness can be from about 5 μm to about 10 μm, or from about 10 μm to about 15 μm (in dry state).

As noted above, the diffusion barrier includes a block copolymer, such as a single block copolymer having at least one hydrophilic block and at least one hydrophobic block. The block copolymer can include an alternating sequence of blocks (i.e., a hydrophilic block is linked to a hydrophobic block). The hydrophilic and hydrophobic blocks are covalently linked to each other within a polymer molecule. The average molecular weight of the polymer (by weight) can be from about 20 kD to about 70 kD, from about 25 kD to about 60 kD, or from about 30 kD to about 50 kD. The molar ratio of the hydrophilic to hydrophobic portions in the block copolymer can be from about 75% (hydrophilic):25% (hydrophobic) to about 25% (hydrophilic):75% (hydrophobic), from about 65% (hydrophilic):35% (hydrophobic) to about 35% (hydrophilic):65% (hydrophobic), or from about 60% (hydrophilic):40% (hydrophobic) to about 40% (hydrophilic):60% (hydrophobic).

A hydrophilic block of the block copolymer can be of at least about 90%, at least about 95%, or completely of hydrophilic monomeric units. It can have a length of from about 50 to about 400 monomeric molecules, from about 50 to about 200 monomeric molecules, from about 150 to about 300 monomeric molecules, from about 100 to about 150 monomeric molecules, or from about 200 to about 250 monomeric molecules.

A hydrophobic block of the block copolymer can be of at least about 90%, at least about 95%, or completely of hydrophobic monomeric units. It can have a length of from about 50 to about 300 monomeric units, from about 50 to about 200 monomeric units, from about 150 to about 250 monomeric units, from about 80 to about 150 monomeric units, or from about 170 to about 200 monomeric units.

The hydrophilic blocks and/or the hydrophobic blocks can be (meth)acrylic-based units. Alternatively, both the hydrophilic blocks and the hydrophobic blocks can be (meth)acrylic-based monomeric units.

In some embodiments, the hydrophilic monomeric units of the hydrophilic block can be hydrophilic (meth)acryl esters (i.e., esters with a polar, i.e., OH, $OCH_3$ or $OC_2H_5$ group within the alcohol portion of the ester), hydrophilic (meth)acrylamides with an amide ($NH_2$), or an N-alkyl- or N,N-dialkylamide group, where the alkyl group includes 1-3 C-atoms and optionally hydrophilic groups such as OH, $OCH_3$ or $OC_2H_5$, and suitable (meth)acrylic units having a charged (e.g., an anionic or cationic) group, such as acrylic acid (acrylate) or methacrylic acid (methacrylate). Further, combinations of monomeric units may be employed.

Specific monomeric units for the hydrophilic block include the following:
2-hydroxyethyl acrylate;
2-hydroxyethyl methacrylate (HEMA);
2-methoxyethyl acrylate;
2-methoxyethyl methacrylate;
2-ethoxyethyl acrylate;
2-ethoxyethyl methacrylate;
2- or 3-hydroxypropyl acrylate;
2- or 3-hydroxypropyl methacrylate (2- or 3-HPMA);
2- or 3-methoxypropyl acrylate;
2- or 3-methoxypropyl methacrylate;
2- or 3-ethoxypropyl acrylate;
2- or 3-ethoxypropyl methacrylate;
1- or 2-glycerol acrylate;
1- or 2-glycerol methacrylate;
acrylamide;
methacrylamide;
an N-alkyl- or N,N-dialkyl acrylamide; and
an N-alkyl- or N,N-dialkyl methylamide, wherein alkyl comprises 1-3 C-atoms such as methyl, ethyl or propyl, acrylic acid (acrylate), methacrylic acid (methacrylate) and combinations thereof.

Other hydrophilic monomers include 2-hydroxyethyl methacrylate (HEMA) and/or 2- or 3-hydroxypropyl methacrylate (2- or 3-HPMA). In some embodiments, the hydrophilic block has at least two different hydrophilic monomeric units. For example, it may be a random copolymer of at least two different hydrophilic monomeric units such as HEMA and 2-HPMA.

To introduce ionic groups into the monomer, charged monomeric units, such as acrylic acid (acrylate) and/or methacrylic acid (methacrylate), can be incorporated into the hydrophilic block. Thus, in one embodiment, the hydrophilic block can be made from at least one non-ionic hydrophilic monomeric unit (e.g., as described above) and from at least one ionic hydrophilic monomeric unit, where the ionic monomeric unit is present in a molar amount of about 1 mole-% to about 20 mole-%. When the hydrophilic block includes an ionic monomeric unit, such as acrylic acid or methacrylic acid, copolymerization with a hydrophilic monomer such as (meth)acrylamide, particularly N,N-dialkyl acryl- or methacrylamides.

In some embodiments, the hydrophobic monomeric units of the hydrophobic block can be selected from hydrophobic acrylic and/or methacrylic units, styrene-based monomeric units, or combinations thereof. Alternatively, the hydrophobic monomeric units can be hydrophobic (meth)acryl esters (e.g., esters having an alcohol portion with 1-3 C-atoms without hydrophilic group).

Specific monomeric units for the hydrophobic block include the following:
methyl acrylate;
methyl methacrylate (MMA);
ethyl acrylate;
ethyl methacrylate (EMA);
n- or i-propyl acrylate;
n- or i-propyl methacrylate;
n-butyl acrylate;
n-butyl methacrylate (BUMA);
neopentyl acrylate; and
neopentyl methacrylate, and combinations thereof.

In other embodiments the hydrophobic block can include at least two different hydrophobic monomeric units, which are, for example, present as a random copolymer. In one embodiment, the hydrophobic block includes methyl methacrylate (MMA) and n-butyl methacrylate (BUMA). Alternatively, the hydrophobic block can be a random copolymer of MMA and BUMA, where the molar ratio between MMA and BUMA is from about 60% (MMA):40% (BUMA) to about 40% (MMA):60% (BUMA), or from about 50% (MMA):50% (BUMA). The glass transition temperature (Tg) of the hydrophobic block is about 100° C. or less, about 90° C. or less, or about 80° C. or less. Alternatively, the Tg is about 40° C. to about 80° C. In certain embodiments, the hydrophobic block can include styrenic units having a Tg of about 95° C.

The block copolymers described herein can be manufactured according to known methods, such as the method disclosed in Böker et al. (2001) *Macromolecules* 34:7477-7488.

The block copolymers can be applied to the electrode system by usual techniques such as, for example, by providing a solution of the block copolymer in a suitable solvent or solvent mixture (e.g., an organic solvent, such as ether), which is applied to the prefabricated electrode system and dried thereon.

When the block copolymer is contacted with water, it shows a water uptake of about 15% to about 30% by weight (based on the polymer dry weight) at a temperature of about 37° C. and a pH of about 7.4 (e.g., an aqueous phosphate buffer 10 mM $KH_2PO_4$, 10 mM $NaH_2PO_4$ and 147 mM NaCl).

In addition to the block copolymer, the diffusion barrier also can include additional components, particularly non-polymeric components, which may be dispersed and/or dissolved in the polymer. These additional components include plasticizers, particularly biocompatible plasticizers, such as tri-(2-ethylhexyl) trimellitate and/or glycerol.

Advantageously, the diffusion barrier has a high effective diffusion coefficient ($D_{eff}$) for glucose, which can be $\geq 10^{-10}$ cm$^2$/s, $\geq 5 \cdot 10^{-10}$ cm$^2$/s, or $\geq 10^{-9}$ cm$^2$/s, and can be up to about $10^{-7}$ or $10^{-8}$ cm$^2$/s at a temperature of about 37° C. and a pH of about 7.4. The $D_{eff}$ may be determined as described below in Example 4 according to the following equation:

$$D_{eff} = SE_m / F \cdot L_m \cdot 5182 \cdot 10^{-8}$$

where $SE_m$ is the sensitivity of the WE, F is the area of the WE, and $L_m$ is the layer thickness of the diffusion barrier. $SE_m$ and $L_m$ can be determined as described below in the Examples.

The electrode system therefore can be used for measuring the concentration of an analyte under in vivo conditions (i.e., when inserted or implanted into a body). The analyte may be any molecule or ion present in tissue or body fluid such as, for example, oxygen, carbon dioxide, salts (cations and/or anions), fats or fat components, carbohydrates or carbohydrate components, proteins or protein components, or other type of biomolecules. The electrode system is particularly useful for the concentration of analytes that can be efficiently transferred between body fluid (e.g., blood) and tissue such as oxygen, carbon dioxide, sodium cations, chloride anions, glucose, urea, glycerol, lactate and pyruvate.

The electrode system also includes an enzyme immobilized on an electrode, such as the WE, as an enzyme layer, where the enzyme is suitable for determining concentration a desired analyte. In one embodiment, the enzyme is capable of catalytically converting the analyte, thereby generating an electric signal detectable by the electric conductor of the WE. The enzyme can be an oxidase such as, for example, glucose oxidase or lactate oxidase. Alternatively, the enzyme can be a dehydrogenase such as, for example, a glucose dehydrogenase or a lactate dehydrogenase.

In addition to the enzyme, the enzyme layer also can include an electrocatalyst or a redox mediator that favors transfer of electrons to conductive components of the WE (e.g., graphite particles). Suitable electrocatalysts include metal oxides such as manganese dioxide or organo-metallic compounds such as cobalt phthalo-cyanine. In one embodiment, the redox mediator can degrade hydrogen peroxide, thereby counteracting depletion of oxygen in the surroundings of the WE. In another embodiment, the redox mediator can be covalently bound to the enzyme, thereby effecting direct electron transfer to the WE. Suitable redox mediators for direct electron transfer include prosthetic groups, such as pyrrolo quinoline quinone (PQQ), flavine adenine dinucleotide (FAD) or other known prosthetic groups. Enzymes can be immobilized on electrodes according to known methods, such as, for example, the method disclosed in Int'l Patent Application No. WO 2007/147475.

In one embodiment, the electrode system includes a counter electrode (CE) with an electrical conductor and a WE with an electrical conductor on which the enzyme layer and the diffusion barrier are arranged. The enzyme layer can be in the form of multiple fields that are arranged on the conductor of the WE at a distance of at least about 0.3 mm, at least about 0.4 mm, or at least about 0.5 mm from each other. The individual fields of the WE can form a series of individual WEs. Between these fields, the conductor of the WE can be covered by an insulation layer. By arranging the fields of the enzyme layer on the top of openings of an electrically insulating layer, the signal-to-noise ratio can be improved. Such arrangements are known and are described in, for example, Int'l Patent Application No. WO 2010/028708.

The electrode system can further include a reference electrode (RE) capable of supplying a reference potential for the WE (e.g., an Ag/Ag—Cl RE). Moreover, the electrode system can include additional counter and/or WEs.

The electrode system may be part of a sensor, for example, by being connected to a potentiostat 10 and an amplifier 11 for amplifying measuring signals of the electrode system. In one embodiment, the sensor can be an enzymatic non-fluidic (ENF) sensor, such as an electrochemical ENF sensor. The electrodes of the electrode system can be arranged on a substrate that carries the potentiostat 10 or can be attached to a circuit board that carries the potentiostat 10.

Another aspect includes a method of using a block copolymer having at least one hydrophilic block and at least one hydrophobic block as a diffusion barrier for an enzymatic electrode, such as the block copolymer described above (e.g., a single block-copolymer). The method also includes using a diffusion barrier and an enzymatic electrode as described above.

These and other advantages, effects, features and objects of the invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
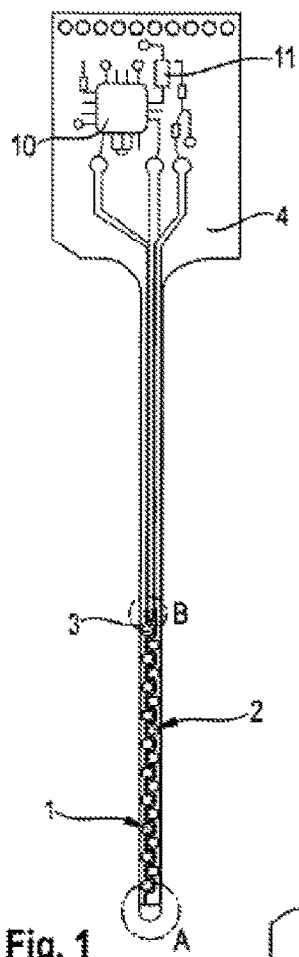
FIG. 1 shows an exemplary embodiment of an electrode system as described herein.

While the present invention is susceptible to various modifications and alternative forms, exemplary embodiments thereof are shown by way of example in the drawings and are herein described in detail. It should be understood, however, that the description of exemplary embodiments that follows is not intended to limit the invention to the particular forms disclosed, but on the contrary, the intention is to cover all advantages, effects, features and objects falling within the spirit and scope of the invention as defined by the embodiments above and the claims below. Reference should therefore be made to the embodiments above and claims below for interpreting the scope of the invention. As such, it should be noted that the embodiments described herein may have advantages, effects, features and objects useful in solving other problems.

DESCRIPTION OF PREFERRED EMBODIMENTS

The systems, sensors and methods now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the systems, sensors and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Systems, Sensors and Methods

Figure 2:
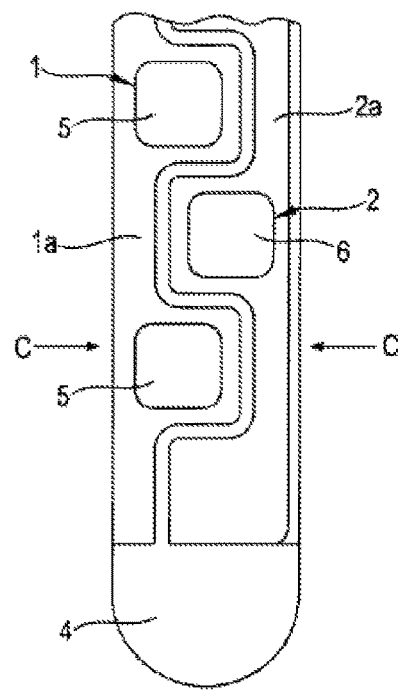
FIG. 2 shows a detail view of FIG. 1.
Figure 3:
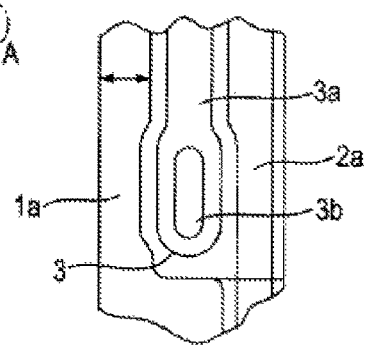
FIG. 3 shows another detail view of FIG. 1.
Figure 4:
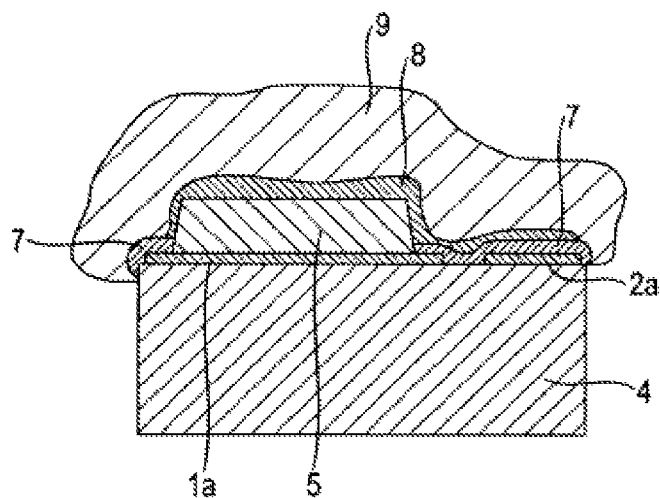
FIG. 4 shows a section along the section line CC of FIG. 2.

FIG. 1 shows an exemplary embodiment of an electrode system for insertion or implantation into body tissue of a human or animal such as, for example, into cutis or subcutaneous fatty tissue. A magnification of detail view A is shown in FIG. 2, and a magnification of detail view B is shown in FIG. 3. FIG. 4 shows a corresponding sectional view along the section line, CC, of FIG. 2.

The electrode system shown has a WE 1, a CE 2, and a RE 3. Electrical conductors of the electrodes 1*a*, 2*a*, 3*a* are arranged in the form of metallic conductor paths and may be made of palladium (Pd) or gold (Au), on a substrate 4. In the embodiment shown, the substrate 4 is a flexible plastic plate made of, for example, polyester. The substrate 4 can be less than about 0.5 mm thick, for example, about 100 µm to about 300 µm, and therefore is easy to bend such that it can adapt to movements of surrounding body tissue after its insertion. As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art. The substrate 4 has a narrow shaft for insertion into body tissue of a patient and a wide head for connection to an electronic system that is arranged outside the body. The shaft of the substrate 4 can be at least about 1 cm in length or alternatively about 2 cm to about 5 cm.

In the embodiment shown, one part of the measuring facility, namely the head of the substrate, can project from the body of the individual during use. Alternatively, it is feasible just as well, though, to implant the entire measuring facility and transmit measuring data in a wireless fashion to a receiver that is arranged outside the individual's body.

The WE 1 carries an enzyme layer 5 that contains immobilized enzyme molecules for catalytic conversion of the analyte. The enzyme layer 5 can be applied, for example, in the form of a curing paste of carbon particles, a polymeric binding agent, a redox mediator or an electro-catalyst, and enzyme molecules. Details on producing an enzyme layer 5 of this type are disclosed in, for example, Int'l Patent Application No. WO 2007/147475.

In the embodiment shown, the enzyme layer 5 is not applied continuously on the conductor 1a of the WE 1, but rather in the form of individual fields that are arranged at a distance from each other. The individual fields of the enzyme layer 5 can be arranged in a series.

The conductor 1a of the WE 1 has narrow sites between the enzyme layer fields that are seen particularly well in FIG. 2. The conductor 2a of the CE 2 has a contour that follows the course of the conductor 1a of the WE 1. This means results in an intercalating or interdigitated arrangement of WE 1 and CE 2 with advantageously short current paths and low current density.

To increase its effective surface, the CE 2 can be provided with a porous electrically conductive layer 6 that is situated in the form of individual fields on the conductor 2a of the CE 2. Like the enzyme layer 5 of the WE 1, this layer 6 can be applied in the form of a curing paste of carbon particles and a polymeric binding agent. The fields of the layer 6 preferably have the same dimensions as the fields of the enzyme layer 5, although this is not obligatory. However, measures for increasing the surface of the CE can just as well be foregone, and the CE 2 can just as well be designed to be a linear conductor path with no coatings of any kind, or with a coating made from the described block copolymer and optionally a spacer.

The RE 3 is arranged between the conductor 1a of the WE 1 and the conductor 2a of the CE 2. The RE 3 shown in FIG. 3 consists of a conductor 3a on which a field 3b of conductive silver/silver chloride (Ag/Ag—Cl) paste is arranged.

FIG. 4 shows a schematic sectional view along the section line, CC, of FIG. 2. The section line, CC, extends through one of the enzyme layer fields 5 of the WE 1 and between the fields of the conductive layer 6 of the CE 2. Between the fields of enzyme layer 5, the conductor 1a of the WE 1 can be covered with an electrically insulating layer 7, like the conductor 2a of the CE 2 between the fields of the conductive layers 6, to prevent interfering reactions that may otherwise be catalyzed by the metal of the conductor paths 1a, 2a. The fields of the enzyme layer 5 therefore are situated in openings of the insulation layer 7. Likewise, the fields of the electrically conductive layer 6 of the CE 2 also may be placed on top of openings of the insulating layer 7.

The enzyme layer 5 is covered by a cover layer 8 that presents a diffusion resistance to the analyte to be measured and therefore acts as a diffusion barrier. The cover layer 8 consists of a single copolymer with alternating hydrophilic and hydrophobic blocks as described above.

The thickness of the cover layer 8 can be, for example, about 3 µm to about 30 µm, particularly from about 5 µm to about 10 µm or from about 10 µm to about 15 µm. Because of its diffusion resistance, the cover layer 8 causes fewer analyte molecules to reach the enzyme layer 5 per unit of time. Accordingly, the cover layer 8 reduces the rate at which analyte molecules are converted, and therefore counteracts a depletion of the analyte concentration in surroundings of the WE.

The cover layer 8 extends continuously essentially over the entire area of the conductor 1a of the WE 1. On the cover layer 8, a biocompatible membrane may be arranged as spacer 9 that establishes a minimal distance between the enzyme layer 5 and cells of surrounding body tissue. This means advantageously generates a reservoir for analyte molecules from which analyte molecules can get to the corresponding enzyme layer field 5 in case of a transient disturbance of the fluid exchange in the surroundings of an enzyme layer field 5. If the exchange of body fluid in the surroundings of the electrode system is transiently limited or even prevented, the analyte molecules stored in the spacer 9 keep diffusing to the enzyme layer 5 of the WE 1 where they are converted. The spacer 9 therefore causes a notable depletion of the analyte concentration and corresponding falsification of the measuring results to occur only after a significantly longer period of time. In the embodiment shown, the membrane forming the spacer 9 also covers the CE 2 and the RE 3.

The spacer membrane 9 can be, for example, a dialysis membrane. As used herein, "dialysis membrane" and the like means a membrane that is impermeable for molecules larger than a maximal size. The dialysis membrane can be prefabricated in a separate manufacturing process and then may be applied during the fabrication of the electrode system. The maximal size of the molecules for which the dialysis membrane is permeable is selected such that analyte molecules can pass, while larger molecules are retained.

Alternatively, instead of a dialysis membrane, a coating made of a polymer that is highly permeable for the analyte and water, for example, on the basis of polyurethane or of acrylate, can be applied over the electrode system as spacer membrane 9.

The spacer membrane 9 can made from a copolymer of (meth)acrylates. In some instances, the spacer membrane 9 is a copolymer from at least 2 or 3 (meth)acrylates. In some instances, the spacer membrane 9 can be more than about 50 mol-%, at least about 60 mol-% or at least about 70 mol-% hydrophilic monomer units (e.g., HEMA and/or 2-HPMA), and up to about 40 mol-% or up to about 30 mol-% hydrophilic units (e.g., BUMA and/or MMA). The spacer membrane 9 may be a random or block copolymer. In some instances, spacer membrane 9 comprises MMA or BUMA as hydrophobic moieties and 2-HEMA and/or 2-HPMA as hydrophilic moieties. The spacer membrane 9 is highly permeable for the analyte (i.e., it does significantly lower the sensitivity per area of the WE), for example, about 20% or less, or about 5% or less, with a layer thickness of less than about 20 µm or less than about 5 µm. In certain embodiments, the thickness of the spacer membrane 9 is from about 1 µm to about 3 µm.

The enzyme layer 5 of the electrode system can contain metal oxide particles, such as manganese dioxide particles, as catalytic redox mediator. Manganese dioxide catalytically converts hydrogen peroxide that is formed, for example, by enzymatic oxidation of glucose and other bioanalytes. During the degradation of hydrogen peroxide, the manganese dioxide particles transfer electrons to conductive components of the WE 1, for example, to graphite particles in the enzyme layer 5. The catalytic degradation of hydrogen peroxide counteracts any decrease of the oxygen concentration in the enzyme layer 5. Advantageously, this allows conversion of the analyte to be detected in the enzyme layer 5 to not be limited by the local oxygen concentration. The use of the catalytic redox mediator therefore counteracts a falsification of the measuring result by the oxygen concentration being low. Another advantage of a catalytic redox mediator is that it prevents the generation of cell-damaging concentrations of hydrogen peroxide.

A spacer membrane polymer as described herein may be used as an outer coating for a diffusion barrier, but also as an outer coating of an electrode system in general, particularly of an electrode system for measuring the concentration of an analyte under in vivo conditions, comprising an electrode with immobilized enzyme molecules and a diffusion barrier that controls diffusion of the analyte from the exterior of the electrode system to the enzyme molecules.

Thus, it is a further object of the present disclosure to provide an electrode system for measuring the concentration of an analyte under in vivo conditions, where the system includes an electrode with immobilized enzyme molecules and a diffusion barrier that controls diffusion of the analyte form the exterior of the electrode system to the enzyme molecules, where a spacer membrane forms at least a portion of the outer layer of the electrode system, where the spacer membrane includes a hydrophilic copolymer of acrylic and/or methacrylic monomers, and where the polymer comprises more than about 50 mol-% hydrophilic monomers.

The features of this embodiment, particularly with regard to the structure of the electrode system, the analyte and the enzyme molecules, are as described herein. The diffusion barrier is as described herein; however, it also may have a different composition or may be absent. Acrylic and methacrylic monomers of the spacer membrane copolymer are as described herein. The outer spacer membrane can cover at least the WE portion including the enzyme molecules and optionally also other portions such as, for example, the CE.

EXAMPLES

The invention will be more fully understood upon consideration of the following non-limiting examples, which are offered for purposes of illustration, not limitation.

Example 1: Permeability of an Enzymatic Non-Fluidic (ENF) Glucose Sensor with Distributed Electrodes for Transcutaneous Implantation Having a Diffusion Layer Consisting of One Single Block Copolymer A sensor was built on a prefabricated palladium strip conductor structure on a polyester substrate having a thickness of 250 µm. The WE and CE were arranged distributedly as shown in FIGS. 1-2.

The fields of the CE were overprinted with carbon paste, the rest of the strip conductor was insulated. The fields of the WE were overprinted with a mixture of cross-linked glucose oxidase (enzyme), conductive polymer paste and electric catalyst, here manganese(IV)-oxide (Technipur). The remaining paths of the strip conductor were again insulated. The RE consists of Ag/AgCl paste. The electrodes cover about 1 cm of the sensor shaft.

The WE-fields were coated with a block copolymer diffusion layer consisting of a HEMA block and a BUMA block. The thickness of the layer is 7 µm.

Four sensor batches were produced, each provided with a specific block copolymer as diffusion layer (see list hereinbelow). All block copolymers were obtained from Polymer Source (Montreal) and are listed in the following Table 1.

TABLE 1

Block Copolymers.

| Name Copolymer | Molecular Ratio/% BUMA/HEMA | Monomeric units HEMA | Molecular weight Copolymer [kD] |
|---|---|---|---|
| C | 73/27 | 92 | 47 |
| F | 60/40 | 108 | 37 |
| D | 48/52 | 162 | 44 |
| B | 62/38 | 169 | 61 |

The respective block copolymer was dissolved in organic solvent (25% concentration), and the sensors were coated therewith. After drying by means of belt driers (2 min, 30° C. to 50° C.), the coated sensors were tested in vitro in glucose solutions of different concentrations. Of each sensor batch, 10 sensors were measured as random sample. As a measure for the in vitro sensitivity, the signal was calculated by the difference of the measured currents at 10 mM and 0 mM glucose concentration, which then was divided by 10 mM (cf. Example 4).

Figure 5:
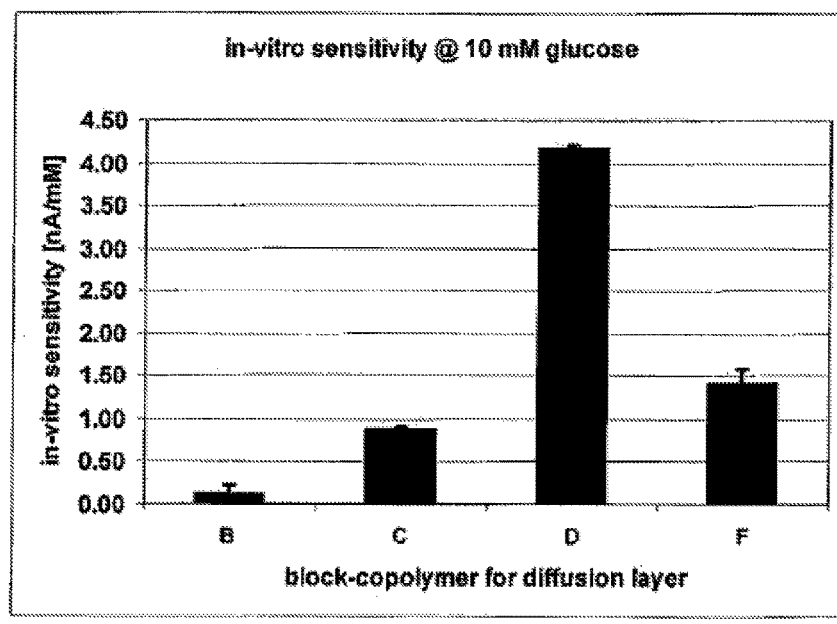
FIG. 5 shows sensitivity (with standard deviation) of four glucose sensors (at 10 mM glucose) provided with different block polymers (C, F, D, B) as diffusion barrier layers.

All sensors were operated at a polarization voltage of 350 mV versus Ag/AgCl, and the measured temperature was kept constant at 37° C. The sensors used for the measurement series did not comprise the spacer as described in WO 2010/028708 which, however, did not make any difference in view of the tested signal level. FIG. 5 shows the sensor sensitivity with standard deviations for the four different diffusion layers.

Concerning block copolymers C, D and F, there is a clear connection between in vitro sensitivity and molar ratio of hydrophobic block compared to hydrophilic block. At about identical total chain length of the copolymer, the sensitivity increases as the amount of hydrophilic block (HEMA) increases.

The sensors having a diffusion layer of block copolymer B are an exception. Even though polymer B has a relative ratio of hydrophobic to hydrophilic amount similar to polymer F, the sensitivity and thus the permeability for glucose is reduced. Empirically it can be stated that in case of polymer B the total chain length—corresponding to the molecular weight (total) of the copolymer molecule—is so large that the permeability of the layer is reduced. This also may be seen in the gravimetrically determined water uptake of block copolymer B as compared to the remaining polymers. Polymer B has a water uptake of 10.6%±1.5% (weight percent referred to the polymer dry weight). Polymer C lies at 15.6%±0.0%, polymer F at 16.5±3.1% and polymer D at 27%±1.7%.

Example 2: Mechanic Flexibility of the Diffusion Layer of an ENF Glucose Sensor

The sensor was manufactured as described in WO 2010/028708, however, having a diffusion layer as described herein. It was assumed that the glass transition temperature (Tg) is a substitute parameter for the mechanic flexibility. In addition, it was assumed that the Tg, which may be allocated to the hydrophobic block, determines the mechanic flexibility in in vivo applications. It should be noted that several Tgs may be identified for one block copolymer, corresponding to the number of blocks.

The sensors were coated with the same electrode pastes as above in Example 1. Then, some of the sensors were coated with a copolymer selected from MMA-HEMA (produced by Polymer Source, Montreal). This polymer (called E) has a total molecular weight of 41 kD, the molar ratio of MMA (hydrophobic amount) to HEMA is 60%:40%. The Tg of the hydrophobic block is 111° C., determined by DSC and a heating rate of 10° C./min.

Besides, other sensors were provided with a diffusion layer of a block copolymer of the invention (called A). The hydrophobic block of copolymer A contains MMA and BUMA at equal molar amounts in a randomized sequence. Again, the molar ratio of the hydrophobic part to the hydrophilic part is 60%:40%. The molecular weight is 36 kD. The Tg of the hydrophobic block decreases, due to the randomized sequence of MMA and BUMA (Tg about 45° C.), to 73° C.

Both diffusion layers were generated from the respective solution (25%) of the copolymers in ether and dried as described above in Example 1. The thickness of the diffusion layers was 7 μm. A spacer layer was applied subsequently via dip coating and dried 24 hours at room temperature. The spacer layer was made of Lipidure CM 5206 (NOF; Japan).

After explantation from the tissue, sensors having a copolymer E diffusion layer show sporadic cracks in the diffusion layer. This is taken as an effect of the mechanic load. In contrast thereto, sensors having a copolymer A diffusion layer, do not show any cracks under identical load. This is obviously due to the reduction of Tg, which increases the mechanic stability of the copolymer. A physical mixture of two copolymers, as disclosed in Int'l Patent Application No. WO 2010/028708, is no longer required.

Example 3: Optimized Permeation Behaviour of an ENF Glucose Sensor with Distributed Electrode and Diffusion Layer A sensor was manufactured as described above in Example 1, but with an additional spacer layer on the total of the sensor shaft. Sensors with respective diffusion layer were produced for copolymers A, C, D and F of Examples 1 and 2. For this purpose, a 24% etheric solution of the copolymer was generated. Each solution was applied onto a set of sensors (N=10) and then dried in a band drier. Thereby, diffusion layers having a thickness of 7 μm, were obtained.

Afterwards, the sensors were provided with a spacer layer as described above in Example 2.

Figure 6:
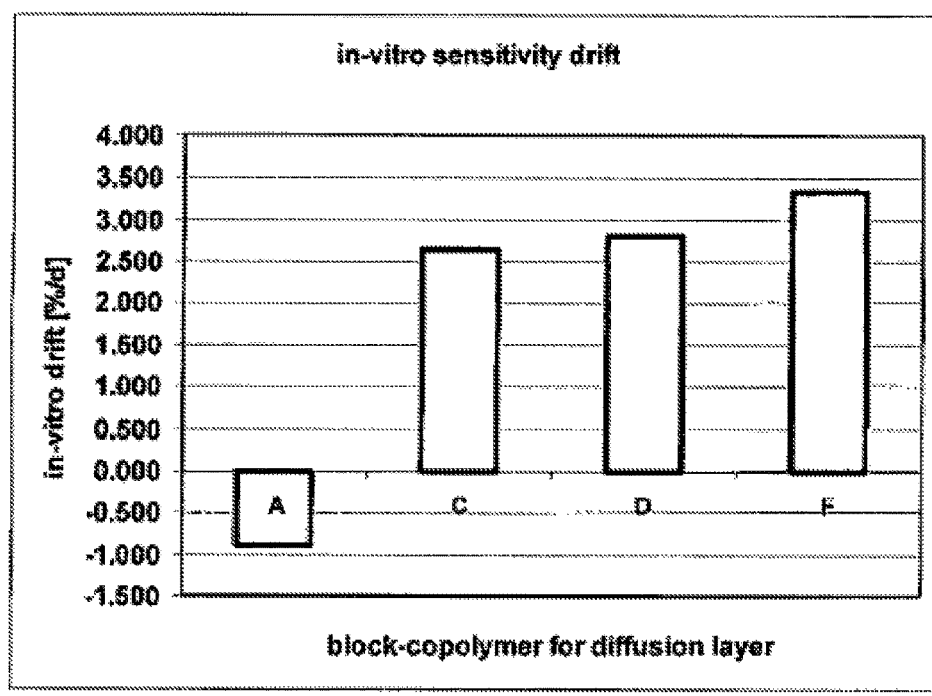
FIG. 6 shows sensor drift of four glucose sensors provided with different block copolymers (A, C, D, F) as diffusion barrier layers.

The sensor was connected with a measuring system on the sensor head, which transfers the measured data to a data store. The in vitro measurements were carried out as above in Example 1, however, over a measuring period of 7 days. From the measured data, the sensitivity drift was calculated over the respective measuring period for each sensor. FIG. 6 shows for each sensor variant (i.e., sensors of a variant of the diffusion layer) the mean value of the in vitro drift value for the group. The initial phase of the measurement—the first 6 hours, the so-called startup phase—was excluded from the calculation.

For all copolymers C, D and F having a hydrophobic block of BUMA, there is a positive drift (i.e., the sensitivity increases according to time). Contrary thereto, copolymer A with the hydrophobic block of a random copolymer of MMA and BUMA, leads to a very low, slightly negative, drift.

These differences may be explained by the long-time permeability response of the respective diffusion layers, which was measured in additional experiments. Palladium sensors without WE-paste, but with a defined active surface (i.e., also without an enzyme layer)—excluding the influence of its swelling behaviour on the results—were coated with the above polymer solutions, and after drying, the thickness of the layer was measured. Subsequently, conductivity was measured in sodium- and chloride-containing buffer solution.

Figure 7:
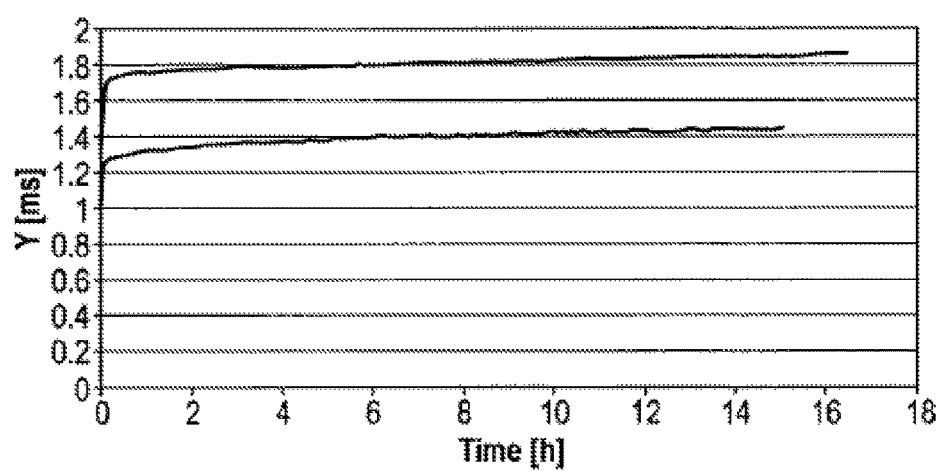
FIG. 7 shows conductivity of block copolymer A dependent on time (2 experiments).

FIG. 7 shows that the conductivity of copolymer A remained nearly constant after a short startup phase.

Figure 8:
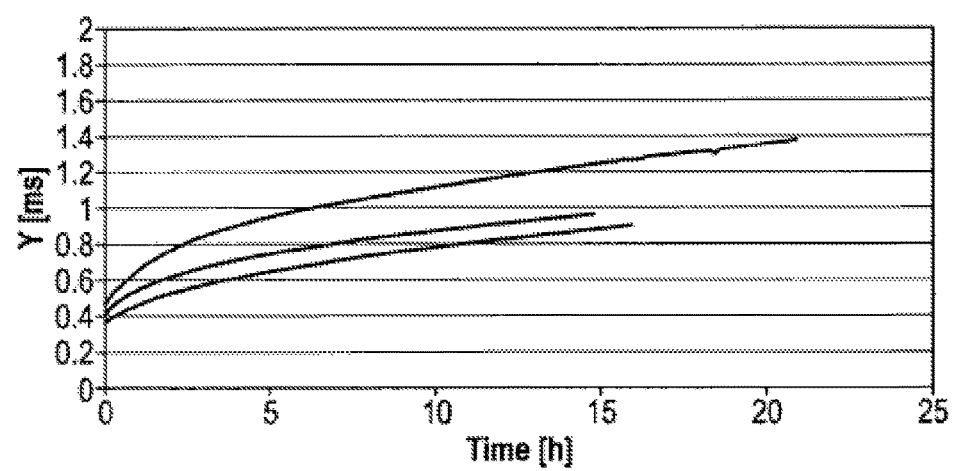
FIG. 8 shows conductivity of block copolymer F dependent on time (3 experiments).

This is not the case for copolymer F, even under identical measurement conditions, as may be seen in FIG. 8. In this case, a long-term and strong permeability response of the diffusion layer of copolymer F was observed, which was practically independent of the layer thickness. For copolymer F—and also copolymers C and D (not shown)—with a hydrophobic block of BUMA, an increase of permeability results even over a long time period. When measured, this leads to a continuous increase of sensitivity if the diffusion layer was applied onto the sensor with distributed enzyme layer. This explains the observed positive sensor drift.

Vice versa, a sensor having block copolymer A, shows a negligible drift, which is due to a very low permeability alteration in the conductivity measurement. Directly after starting measurement (until about 1 hour afterwards); however, a strong increase of conductivity is observed in copolymer A. Here, a very fast startup is observed, which is terminated after about 1 hour. At this time, the diffusion layer is completely wetted and has terminated its structural reorganisation due to water uptake. The extent of the structural change presumably depends on the Tg. It seems plausible that a copolymer having an increased Tg passes a reorganisation, which is limited in time and amplitude, as compared to a copolymer having a Tg in the range of the ambient temperature.

In addition, sensors with copolymer A appeared to show a comparatively high sensitivity at the start of measurements as compared to sensors having a copolymer F diffusion layer. This is to be expected due to the identical relative ratios between hydrophobic and hydrophilic blocks. The achieved sensitivity range of 1 nA/mM to 1.5 nA/mM (see, Example 1) is deemed ideal. This sensitivity is likewise obtained for sensors having a diffusion layer consisting of copolymer A.

Regarding the sum of the three physico-chemical characteristics—permeability, mechanic stability and permeability response—an optimal sensor may preferably be obtained with a diffusion layer of a block copolymer, having a hydrophobic block with at least two different randomly arranged hydrophobic monomeric units, such as block copolymer A. None of the other block copolymers, whose hydrophobic blocks only consist of a single monomeric unit reaches a quality, which could be compared in all three parameters with copolymer A.

Example 4: Characterization of Block Copolymers

A multiple field sensor (10 fields of WEs and CEs, respectively) for the continuous measurement of the glucose was produced and characterized in vitro.

The sensor was provided with a diffusion layer consisting of a block copolymer comprising a hydrophobic block of random copolymerized methyl methacrylate (MMA) and n-butyl methacrylate (BUMA) and a hydrophilic block of 2-hydroxyethyl methacrylate (HEMA). These polymers (specified G and H) were produced by Polymer Source (Montreal) and are more permeable than polymer A from Examples 1-3.

TABLE 2

Additional Copolymer Details.

| Polymer | G | H | A |
|---|---|---|---|
| Molecular weights (Mn [kD]) | 23.5-b-29 | 21-b-20.5 | 21-b-15 |
| Weight-% HEMA | 55.2 | 49.4 | 41.6 |
| Mol-% HEMA (stoichiometrically) | 53.5 | 47.4 | 40 |
| Mol-% HEMA (measured by $^1$H, $^{13}$C NMR) | 51 | 46 | 32.6 |
| Tg [° C.] hydrophobic block | 65 | 68 | 86 |
| HEMA monomeric units | 223 | 157 | 115 |
| MMA monomeric units | 194 | 174 | 174 |

The molecular weights (Mn) of each block are separately indicated above in Table 2 and represent average values, as polymers are known to have distributions of molecular chain lengths around a specified mean value. This also applies to the derived quantities in Table 2.

The indicated Tg of the hydrophobic block are within the desired range in to guarantee mechanical flexibility.

The decisive parameter with regard to the permeability of the diffusion barrier for the analyte is the sensitivity per area unit of the WE (i.e., the geometric area). The sensitivity SE was calculated from current (I) measurements at 10 mM and at 0 mM glucose concentration in phosphate-buffered solution (pH 7.4) in nA/mM:

$$SE = [I(10\ mM) - I(0\ mM)]/10$$

for each of the analyzed sensors. From the individual measurement values (N=8) the mean sensitivity $SE_m$ was determined. The obtained sensitivity values were divided by the microscopically measured geometric total area F of all WE spots on the multi-field sensor. Thereby, a sensitivity density $SE_m/F$ was obtained.

The linearity Y of the in vitro function curve is an indication of the diffusion control functionality of the polymer cover layer on the WE. It was calculated from current measurements at 20 mM, 10 mM and 0 mM glucose concentration in %:

$$Y^{20\ mM} = 50 \cdot [I(20\ mM) - I(0\ mM)] / [I(10\ mM) - I(0\ mM)]$$

for each of the analyzed sensors. From the individual measurement values the mean linearity value and its standard deviation were determined (cf. Table 3).

Finally, the layer thickness L of the diffusion barrier of the sensors was determined by optical measurement for each of the polymers. The corresponding mean values were computed for a sample of ≥23 sensors with the same polymer. Therefrom, the effective diffusion coefficient $D_{eff}$ of the cover layer may be calculated:

$$D_{eff} = SE_m / F \cdot L_m \cdot 5.182 \cdot 10^{-8}$$

in cm$^2$/s, wherein $SE_m$ and $L_m$ are the respective mean values for the sensitivity and the layer thickness, and F is the total area of all WE spots.

Figure 9:
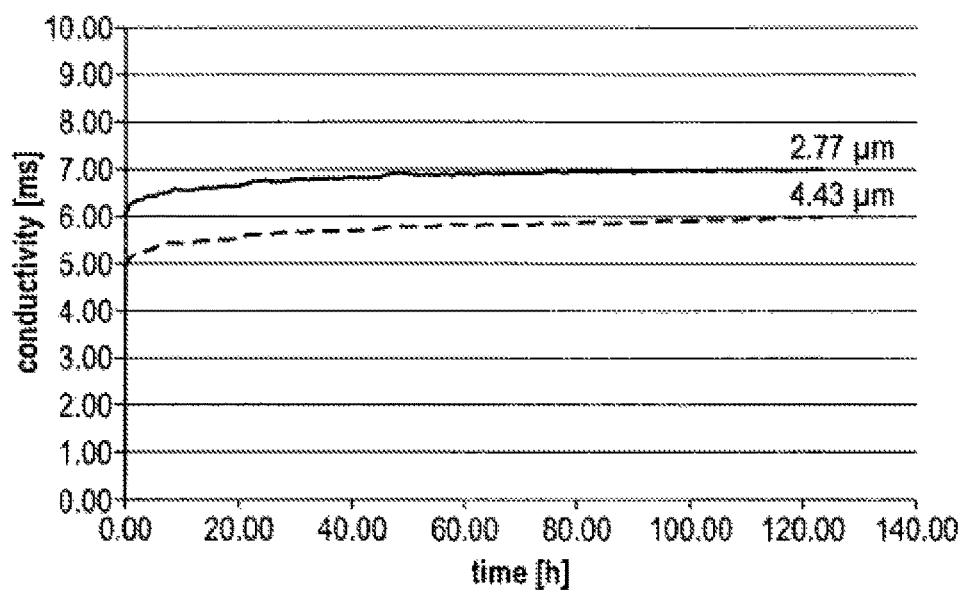
FIG. 9 shows conductivity of block copolymer H dependent on time for a layer thickness of 2.77 µm or 4.43 µm, respectively.

The sensor drift was calculated from repetitions of the glucose concentration stages over 7 days of in vitro measurements. The results for polymer H showing a substantially constant conductivity are depicted in FIG. 9.

TABLE 3

Results of the Functional Characterization.

| | Polymer | |
|---|---|---|
| | G | H |
| $SE_m/F$ [nA/mM * mm$^2$)] | 1.85 | 1.25 |
| Drift [% d] | −1.5 ± 0.2 | 0.3 ± 0.1 |
| $Y^{20mM}$ [%] | 88.2 ± 0.7 | 88.6 ± 0.3 |
| Layer Thickness $L_m$ [μm] | 11.61 | 12.69 |
| $D_{eff}$ [cm$^2$/s] | 1.11305 * 10$^{-9}$ | 8.22019 * 10$^{-10}$ |

For the more hydrophilic polymer G (which is more permeable for glucose), the diffusion coefficient also was determined with an alternative method, for example, permeation of glucose from a chamber with a glucose solution into a chamber with a glucose-free buffer through a film of the polymer. According to this method, a similar value for the diffusion coefficient was obtained (1.17·10$^{-9}$ cm$^2$/s).

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

LISTING OF REFERENCE NUMBERS

1. Working electrode
1a. Electrical conductor of working electrode
2. Counter electrode
2a. Electrical conductor of counter electrode
3. Reference electrode
3a. Electrical conductor of reference electrode
3b. Field or layer of silver/silver chloride (Ag/Ag—Cl)
4. Substrate
5. Enzyme layer
6. Conductive layer
7. Insulating layer
8. Diffusion barrier/cover layer
9. Spacer membrane
10. Potentiostat
11. Amplifier

The invention claimed is:
1. An electrode system for measuring the concentration of an analyte under in vivo conditions, the system comprising:
 an electrode with immobilized enzyme molecules; and
 a diffusion barrier that controls diffusion of the analyte from an exterior of the electrode system to the immobilized enzyme molecules, wherein the diffusion barrier comprises a block copolymer having at least one hydrophilic block and at least one hydrophobic block, wherein the at least one hydrophilic block is made from hydrophilic monomeric units selected from the group consisting of hydrophilic (meth)acrylesters with a polar —OH, —OCH$_3$ or —OC$_2$H$_2$ group, hydrophilic (meth)acrylamides, (meth)acrylic acid, and combinations thereof, wherein the at least one hydrophilic block and the at least one hydrophobic block are covalently linked to one another, and wherein the at least one hydrophobic block has a glass transition temperature between 40° C. and 100° C.

2. The electrode system of claim 1, wherein:
(i) the at least one hydrophilic block of the block copolymer has a length selected from the group consisting of from about 50 to about 200 monomeric units, from about 150 to about 300 monomeric units, from about 100 to about 150 monomeric units, and from about 200 to about 250 monomeric units; and/or
(ii) the at least one hydrophobic block of the block copolymer has a length selected from the group consisting of from about 50 to about 200 monomeric units, from about 150 to about 250 monomeric units, from about 80 to about 150 monomeric units, and from about 170 to about 200 monomeric units.

3. The electrode system of claim 1, wherein (i) if the hydrophilic monomeric units for the at least one hydrophilic block are hydrophilic (meth)acrylesters with a polar —OH, —OCH$_3$ or —OC$_2$H$_2$ group, they are selected from the group consisting of 2-hydroxyethyl acrylate, 2-hydroxyethyl methacrylate (HEMA), 2-methoxyethyl acrylate, 2-methoxyethyl methacrylate, 2-ethoxyethyl acrylate, 2-ethoxyethyl methacrylate, 2- or 3-hydroxypropyl acrylate, 2- or 3-hydroxypropyl methacrylate (2- or 3-HPMA), 2- or 3-methoxypropyl acrylate, 2- or 3-methoxypropyl methacrylate, 2- or 3-ethoxypropyl acrylate, 2- or 3-ethoxypropyl methacrylate, 1- or 2-glycerol acrylate, 1- or 2-glycerol methacrylate, (ii) if the hydrophilic monomeric units for the at least one hydrophilic block are hydrophilic (meth)acrylamides, then they are selected from the group consisting of acrylamide, methacrylamide, an N-alkyl- or N,N-dialkyl acrylamide, and an N-alkyl- or N,N-dialkyl methylamide wherein the alkyl comprises 1-3 C-atoms, (iii) if the hydrophilic monomeric units for the at least one hydrophilic block are (meth)acrylic acid, they are selected from the group consisting of acrylic acid, methacrylic acid, and (iv) combinations of (i) to (iii).

4. The electrode system of claim 1, wherein the at least one hydrophilic block comprises at least two different hydrophilic monomeric units, wherein at least one of the hydrophilic monomeric units is a non-ionic hydrophilic monomeric unit and at least one of the hydrophilic monomeric units is an ionic hydrophilic monomeric unit, and wherein the ionic hydrophilic monomeric unit is present in a molar amount of from about 1 mol-% to about 20 mol-%.

5. The electrode system of claim 1, wherein the at least one hydrophobic block is made from monomeric units selected from the group consisting of hydrophobic (meth)acrylesters, styrene-based monomers, and combinations thereof.

6. The electrode system of claim 5, wherein if the hydrophobic monomeric units for the at least one hydrophobic block are (meth)acrylesters, they are selected from the group consisting of methyl acrylate, methyl methacrylate (MMA), ethyl acrylate, ethyl methacrylate (EMA), n- or i-propyl acrylate, n- or i-propyl methacrylate, n-butyl acrylate, n-butyl methacrylate (BUMA), neopentyl acrylate, neopentyl methacrylate, and combinations thereof.

7. The electrode system of claim 1, wherein the at least one hydrophobic block comprises at least two different hydrophobic monomeric units.

8. The electrode system of claim 7, wherein the at least one hydrophobic block has a glass transition temperature of about 40° C. to about 80° C.

9. The electrode system of claim 1, wherein the molar ratio of hydrophilic block:hydrophobic block is in a range selected from the group consisting of about 75% (hydrophilic):25% (hydrophobic) to about 25% (hydrophilic):75% (hydrophobic), from about 65% (hydrophilic):35% (hydrophobic) to about 35% (hydrophilic):65% (hydrophobic), and from about 60% (hydrophilic):40% (hydrophobic) to about 40% (hydrophilic):60% (hydrophobic).

10. The electrode system of claim 1 further comprising:
a counter electrode having an electrical conductor; and
a working electrode having an electric conductor on which the immobilized enzyme molecules and the diffusion barrier are arranged.

11. The electrode system of claim 10, wherein the immobilized enzyme molecules are present in the form of multiple fields arranged on the conductor of the working electrode at a distance from each other.

12. The electrode system of claim 1, wherein the diffusion barrier forms a layer covering an enzyme layer with a thickness selected from the group consisting of about 2 μm to about 20 μm, of about 5 μm to about 20 μm, and of about 10 μm to about 15 μm.

13. The electrode system of claim 1, wherein an enzyme layer and the diffusion barrier are covered by a spacer, and wherein the spacer is a copolymer of (meth)acrylates comprising more than 50 mol-% hydrophilic monomeric units.

14. The electrode system of claim 1, wherein the diffusion barrier comprises only one block copolymer.

15. The electrode system of claim 1, wherein the diffusion barrier further comprises a plasticizer.

16. The electrode system of claim 1, wherein the diffusion barrier has an effective diffusion coefficient ($D_{eff}$) for glucose selected from the group consisting of $\geq 10^{-10}$ cm$^2$/s, $\geq 5 \cdot 10^{-10}$ cm$^2$/s, and $\geq 10^{-9}$ cm$^2$/s.

17. An insertable or implantable sensor configured for measuring glucose, the sensor comprising:
a flexible and biocompatible substrate;
the electrode system of claim 1 applied on the substrate;
a potentiostat applied on the substrate and in electrical communication with the electrode system; and
an amplifier applied on the substrate and in electrical communication with the electrode system for amplifying measuring signals of the electrode system,
wherein the immobilized enzyme molecules are glucose oxidase or glucose dehydrogenase.

18. A method of making a diffusion barrier for an enzymatic electrode, the method comprising the steps of:
providing a solution of block copolymer in a solvent or a solvent mixture to a prefabricated electrode system having the enzymatic electrode, wherein the block copolymer comprises at least one hydrophilic block and at least one hydrophobic block covalently linked to one another as the block copolymer, and wherein the at least one hydrophilic block is made from hydrophilic monomeric units selected from the group consisting of hydrophilic (meth)acrylesters with a polar —OH, —OCH$_3$ or —OC$_2$H$_2$ group, hydrophilic (meth)acrylamides, (meth)acrylic acid, and combinations thereof; and
drying the solution into the diffusion barrier for the enzymatic electrode, wherein the at least one hydrophobic block has a glass transition temperature between 40° C. and 100° C.

19. The method of claim 18, wherein:
(i) the at least one hydrophilic block of the block copolymer has a length selected from the group consisting of from about 50 to about 200 monomeric units, from about 150 to about 300 monomeric units, from about 100 to about 150 monomeric units, and from about 200 to about 250 monomeric units; and/or (ii) the at least one hydrophobic block of the block copolymer has a length selected from the group consisting of from about 50 to about 200 monomeric units, from about 150 to about 250 monomeric units, from about 80 to about 150 monomeric units, and from about 170 to about 200 monomeric units.

20. The electrode system of claim 7, wherein the at least two different hydrophobic monomeric units are randomly arranged in the at least one hydrophobic block.

21. The electrode system of claim 7, wherein the at least one hydrophilic block is 2-hydroxyethyl methacrylate (HEMA), and wherein the at least one hydrophobic block is methyl methacrylate (MMA) and n-butyl methacrylate (BUMA).

22. The method of claim 18, wherein the at least one hydrophobic block comprises at least two different hydrophobic monomeric units that are randomly arranged.

23. The method of claim 22, wherein the at least one hydrophilic block is 2-hydroxyethyl methacrylate (HEMA), and wherein the at least one hydrophobic block is methyl methacrylate (MMA) and n-butyl methacrylate (BUMA).

24. The electrode system of claim 1 wherein the at least one hydrophobic block is made from hydrophobic monomeric units selected from the group consisting of hydrophobic (meth)acrylesters, styrene-based monomers and combinations thereof.

25. An electrode system for measuring the concentration of an analyte under in vivo conditions, the system comprising:

an electrode with immobilized enzyme molecules; and a diffusion barrier that controls diffusion of the analyte from an exterior of the electrode system to the immobilized enzyme molecules, wherein the diffusion barrier comprises a block copolymer having at least one hydrophilic block and at least one hydrophobic block, wherein the at least one hydrophilic block is made from hydrophilic monomeric units selected from the group consisting of hydrophilic (meth)acrylesters with a polar —OH, —OCH$_3$ or —OC$_2$H$_2$ group, hydrophilic (meth)acrylamides, (meth)acrylic acid, and combinations thereof, wherein the at least one hydrophilic block and the at least one hydrophobic block are covalently linked to one another, and wherein the at least one hydrophobic block is made from hydrophobic monomeric units selected from the group consisting of hydrophobic (meth)acrylesters, styrene-based monomers and combinations thereof.

* * * * *